United States Patent
Van Benthem et al.

(10) Patent No.: US 9,487,602 B2
(45) Date of Patent: Nov. 8, 2016

(54) FURAN BASED RESIN, PROCESS FOR THE PREPARATION THEREOF, AND USE OF THE COMPOUND

(71) Applicants: Rudolfus Antonius Theodorus Maria Van Benthem, Limbricht (NL); Stijn Witters, Lommel (BE)

(72) Inventors: Rudolfus Antonius Theodorus Maria Van Benthem, Limbricht (NL); Stijn Witters, Lommel (BE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/720,375

(22) Filed: Dec. 19, 2012

(65) Prior Publication Data

US 2013/0109822 A1    May 2, 2013

Related U.S. Application Data

(63) Continuation of application No. 12/808,252, filed as application No. PCT/EP2008/067865 on Dec. 18, 2008, now abandoned.

(30) Foreign Application Priority Data

Dec. 18, 2007  (EP) .................................... 07024483

(51) Int. Cl.
*C08F 124/00* (2006.01)
*C07D 307/48* (2006.01)

(52) U.S. Cl.
CPC ........... *C08F 124/00* (2013.01); *C07D 307/48* (2013.01)

(58) Field of Classification Search
CPC ...................................................... C08F 124/00
USPC .......................................... 528/249; 526/270
See application file for complete search history.

(56) References Cited

PUBLICATIONS

Achmatowicz, O. et al., "Total Synthesis of Higher-Carbon Sugars: Synthesis of Methyl 3,4,5-Tri-O-Acetyl-1,7-Dl-O-Benzyl$_{\alpha\text{-}DL\text{-}gluco\text{-}}$Hept-2-Ulopyranoside", Carbohydrate Research, vol. 141 (1985), pp. 67-76.

Kwiatowski, P. et al., "Highly Diastereoselective Friedel-Crafts Reaction of Furans with 8-Phenylmenthyl Glyoxylate", Organicletters, vol. 8, No. 22, (2006), pp. 5045-5048.

*Primary Examiner* — Duc Truong
(74) *Attorney, Agent, or Firm* — Nixon & Vanderhye P.C.

(57) ABSTRACT

The present invention relates to the polymeric reaction product of compounds according to Formula (I) and Formulae (II) or (III). Formula (I) has the following structure:

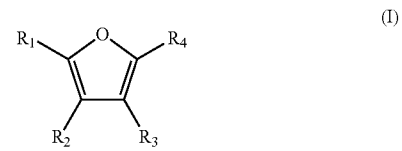

where $R_1$, $R_2$, $R_3$ and $R_4$ are independently H, OH, optionally substituted $C_{1-12}$alkyl, optionally substituted $C_{1-12}$alkenyl, $C_{1-12}$aldehyde, $C_{3-12}$acetals, $C_{2-12}$ ether, and/or $C_{2-12}$ ester; where optionally at least one of $R_1$, $R_2$, $R_3$ and $R_4$ is H. Formulae (II) and (III) have the following structure:

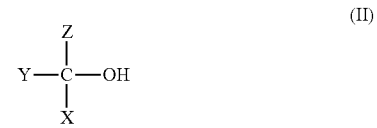

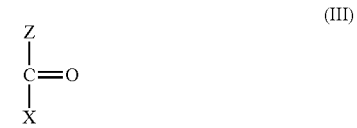

where X is H or $C_{1-4}$alkyl; Y is OH or $OR_5$ where $R_5$ is $C_{1-12}$alkyl, $C_{3-12}$aryl, $C_{4-12}$aralkyl or $C_{3-12}$cycloalkyl; and Z is an electron-withdrawing group.

12 Claims, No Drawings

FURAN BASED RESIN, PROCESS FOR THE PREPARATION THEREOF, AND USE OF THE COMPOUND

This application is a divisional of commonly owned U.S. application Ser. No. 12/808,252, filed Oct. 14, 2010 (now abandoned), which is the national phase application under 35 USC §371 of PCT/EP2008/067865, filed Dec. 18, 2008 which designated the US and claims benefit of EP 07024483.5, filed Dec. 18, 2007, the entire contents of each of which are hereby incorporated by reference.

The invention relates to a resin based on furan compounds.

Furans are defined as compounds having an aromatic, five-member, heterocyclic ring containing at least one oxygen heteroatom. Examples of such compounds include furfural and furfuryl alcohol which can be used in the production of resins. One common method of producing a resin is to react the furan with formaldehyde. These resins have the advantage of that they come from at least partly biorenewable sources. However, a disadvantage, particularly of formaldehyde adducts, is that their use is associated with health risks relating to the emission of formaldehyde during resin preparation, resin curing and in end products. These perceived risks have led to the proposal of legislation to limit the amount of formaldehyde released.

It is the objective of the present invention to reduce or even eliminate the said disadvantage while still providing compound(s) suitable for the preparation of resins.

The reaction of certain furan compounds with certain glyoxylates have been described in the following documents.

Achmatowicz O. et al "Total synthesis of higher carbon sugars: synthesis of methyl 3.4.5-tri-o-acetyl-1,7-di-o-benzyl-alpha-di-gluco-hept-2-ulopyranoside", Carbohydrate Research, vol. 141, 1985, pages 67-76; describes the reaction of single mono-disperse benzyl furfuryl ethers with butyl glyoxylate in the presence of toluene-para-sulfonic acid to give butyl 2-(5-benzyloxymethyl-2-furyl)glycolate. The reaction product of the process described in this document is a mono-disperse single compound and is not a polydisperse polymeric mixture.

Kwiattowski P., et al, "Highly diastereoselective Friedel Crafts reaction of furans with 8-phenylmethyl glyoxylate"; Organic Letters; vol. 8, no 22, 2006, pages 5045-5048; discloses that certain furan derivatives may react with certain glyoxylate esters in the presence of Lewis acid to give furan-2-yl hydroxyacetic acid esters. These are also single mono-disperse compounds and not polymeric mixtures.

The present invention relates to the polymeric reaction product of compounds according to formula (I) and formula (II) or (III).

Formula (I) has the following structure:

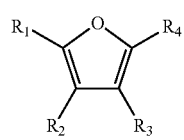
(I)

Where $R_1$, $R_2$, $R_3$ and $R_4$ are independently selected from the group consisting of H, OH and optionally substituted $C_{1-18}$hydrocarbo (optionally further substituted by at least one substituent selected from the group consisting of oxy and carbonyl), where optionally at least one of $R_1$, $R_2$, $R_3$ and $R_4$ is H.

Conveniently $R_1$, $R_2$, $R_3$ and $R_4$ are independently H, OH, substituted or unsubstituted $C_{1-12}$alkyl, substituted or unsubstituted $C_{1-12}$alkenyl, $C_{1-12}$aldehydes, $C_{3-12}$acetals, $C_{2-12}$ethers, $C_{2-12}$esters, where at least one of $R_1$, $R_2$, $R_3$ and $R_4$ is H.

The compound according to any of formulae (I), (II) and/or (III) may be one single compound or a mixture of two or more compounds falling within the scope of the formulae as defined above. Preferably as used herein compound of formulae (I), (II) and/or (III) denotes a plurality of compounds within the scope of these formulae.

Preferably $R_1$, $R_2$, $R_3$ and $R_4$ are independently (subject to the provisos herein) H, OH, substituted or unsubstituted $C_{1-6}$alkyl and/or substituted or unsubstituted $C_{1-6}$alkenyl.

Preferably $R_1$, $R_2$, $R_3$ and $R_4$ are independently (subject to the provisos herein) H, substituted or unsubstituted $C_{1-4}$alkyl and/or substituted or unsubstituted $C_{1-4}$alkenyl.

Preferably $R_1$, $R_2$, $R_3$ and $R_4$ are independently (subject to the provisos herein) H, $C_{1-6}$alkyl, $C_{1-6}$alkenyl, $C_{1-6}$ carboxylic acid (for example carboxy substituted $C_{1-5}$alkyl and/or carboxy substituted $C_{1-5}$alkenyl), hydroxy substituted $C_{1-6}$alkyl, and hydroxy substituted $C_{1-6}$alkenyl.

Preferably $R_1$, $R_2$, $R_3$ and $R_4$ are independently H, —$CH_3$, —$CH_2OH$, —CH=O, and —COOH, where at least one of $R_1$, $R_2$, $R_3$ and $R_4$ is H.

Preferably $R_2$ and $R_3$ are H.

Preferably $R_1$ and $R_4$ are independently H, —$CH_3$— $CH_2OH$, —CH=O and/or —COOH.

Formulae (II) and (III) have the following structure:

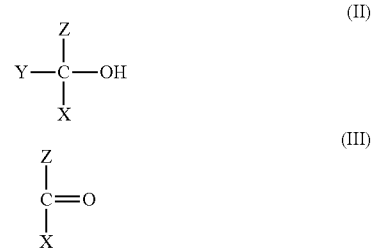

where:
X is selected from the group consisting of H and $C_{1-6}$hydrocarbo;
Y is selected from the group consisting of OH and $OR_5$ where $R_5$ is $C_{1-18}$hydrocarbo; and
Z is an electron-withdrawing group which draws electrons away from the atom to which Z is attached.

The compounds according to the invention suffer less, or even not at all, from the health risks associated with the use of formaldehyde. In addition the present compounds are bio-renewable and have good chemical resistance, and have fire retardant properties. Thus, compounds prepared with the compound according to the present invention are in particular suitable for use in many applications such as adhesives, coatings, laminates, and shaped articles.

In a preferred embodiment of the compound according to the invention, at least one of $R_1$ $R_2$, $R_3$ and $R_4$ is H. This has the advantage that the compound is better suitable for the preparation of the oligomeric or polymeric structures typical for resins. In another preferred embodiment, at least two of $R_1$, $R_2$, $R_3$ and $R_4$ are H. This has the advantage that such a compound can be used to create three-dimensional networks, an ability often desired in resins.

Preferably X is H or $C_{1-4}$alkyl, more preferably H or —$CH_3$.

Preferably Y is —OH or —$OR_5$ where $R_5$ is $C_{1-12}$alkyl, $C_{3-12}$aryl, $C_{4-12}$aralkyl group or $C_{3-12}$cycloalkyl; more preferably is —OH, —$OCH_3$ or —$OCH_2CH_3$.

Z is an electron-withdrawing group (EWG), which draws electrons away from the atom to which Z is attached in the formulae herein. Hydrogen is not an EWG. Suitable electron withdrawing groups for use herein (as Z) are well known to the skilled person. For example EWGs may comprise acid- (e.g. carboxy), ester- (e.g. carbonyloxy), carbonyl, cyano, di-alkylacetal, aldehyde, substituted phenyl, trihalomethyl and/or halo groups. It will be appreciated the specific EWGs that would be suitable for Z in each case will depend on the other substituents attached to the central atom in the formulae II or III herein.

In one embodiment, Z is —C(=O)$OR_6$ wherein $R_6$ is selected from H, $C_{1-12}$alkyl, $C_{3-12}$aryl, $C_{4-12}$aralkyl or $C_{3-12}$cycloalkyl. Preferably $R_6$ is selected from H, $C_{1-12}$alkyl; examples thereof are methyl, ethyl, propyl, butyl, pentyl, hexyl; more preferably, $R_6$ is H, methyl or ethyl.

One preferred group according to formula (II) is:

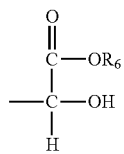

where $R_6$ is as defined herein.

One preferred compound according to formula (II) is:

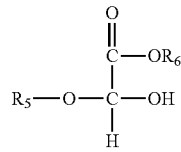

where $R_5$ and $R_6$ are as defined herein.

Another preferred compound according to formula (III) is:

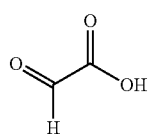

commonly known as glyoxylic acid (GLA).

Examples of preferred compounds according to formula (I) are furan, furfural, furfuryl alcohol, hydroxy methyl furan, bis-hydroxy methyl furan, furandicarboxylic acid, furan carboxylic acid, hydroxymethyl furfunal, hydroxymethyl furan carboxylic acid, combinations thereof and/or mixtures thereof.

Examples of preferred compounds according to formula (II) or (III) include glyoxylic acid, pyruvic acid, methylglyoxylate, ethylglyoxylate, methyl pyruvate, ethyl pyruvate, methylglyoxylate methanol hemiacetal (GMHA™, DSM Fine Chemicals, Linz), ethylglyoxylate ethanol hemiacetal (GEHA™, DSM Fine Chemicals, Linz), ethylglyoxylate methanol hemiacetal, butylglyoxylate butanol hemiacetal, butylglyoxylate methanol hemiacetal, butylglyoxylate ethanol hemiacetal, isopropylglyoxylate isopropanol hemiacetal, propylglyoxylate propanol hemiacetal, cyclohexylglyoxylate methanol hemiacetal, 2-ethylhexylglyoxylate methanol hemiacetal, combinations thereof and/or mixtures thereof.

The terms 'optional substituent' and/or 'optionally substituted' as used herein (unless followed by a list of other substituents) signifies the one or more of following groups (or substitution by these groups): carboxy, sulfo, formyl, hydroxy, amino, imino, nitrilo, mercapto, cyano, nitro, methyl, methoxy and/or combinations thereof. These optional groups include all chemically possible combinations in the same moiety of a plurality (preferably two) of the aforementioned groups (e.g. amino and sulfonyl if directly attached to each other represent a sulfamoyl group). Preferred optional substituents comprise: carboxy, sulfo, hydroxy, amino, mercapto, cyano, methyl, halo, trihalomethyl and/or methoxy.

The term 'hydrocarbo group' as used herein denotes any univalent or multivalent moiety (optionally attached to one or more other moieties) which consists of one or more hydrogen atoms and one or more carbon atoms and may comprise one or more saturated, unsaturated and/or aromatic moieties. Hydrocarbo groups may comprise one or more of the following groups. Hydrocarbyl groups comprise univalent groups formed by removing a hydrogen atom from a hydrocarbon (for example alkyl). Hydrocarbylene groups comprise divalent groups formed by removing two hydrogen atoms from a hydrocarbon, the free valencies of which are not engaged in a double bond (for example alkylene). Hydrocarbylidene groups comprise divalent groups (which may be represented by "$R_2C$=") formed by removing two hydrogen atoms from the same carbon atom of a hydrocarbon, the free valencies of which are engaged in a double bond (for example alkylidene). Hydrocarbylidyne groups comprise trivalent groups (which may be represented by "RC≡"), formed by removing three hydrogen atoms from the same carbon atom of a hydrocarbon the free valencies of which are engaged in a triple bond (for example alkylidyne). Hydrocarbo groups may also comprise saturated carbon to carbon single bonds (e.g. in alkyl groups); unsaturated double and/or triple carbon to carbon bonds (e.g. in respectively alkenyl and alkynyl groups); aromatic groups (e.g. in aryl groups) and/or combinations thereof within the same moiety and where indicated may be substituted with other functional groups The term 'alkyl' or its equivalent (e.g. 'alk') as used herein may be readily replaced, where appropriate and unless the context clearly indicates otherwise, by terms encompassing any other hydrocarbo group such as those described herein (e.g. comprising double bonds, triple bonds, aromatic moieties (such as respectively alkenyl, alkynyl and/or aryl) and/or combinations thereof (e.g. aralkyl) as well as any multivalent hydrocarbo species linking two or more moieties (such as bivalent hydrocarbylene radicals e.g. alkylene).

Any radical group or moiety mentioned herein (e.g. as a substituent) may be a multivalent or a monovalent radical unless otherwise stated or the context clearly indicates otherwise (e.g. a bivalent hydrocarbylene moiety linking two other moieties). However where indicated herein such monovalent or multivalent groups may still also comprise optional substituents. A group which comprises a chain of three or more atoms signifies a group in which the chain wholly or in part may be linear, branched and/or form a ring (including spiro and/or fused rings). The total number of certain atoms is specified for certain substituents for example $C_{1-N}$hybrocarbo, signifies a organo moiety comprising from 1 to N carbon atoms. In any of the formulae herein if one or more substituents are not indicated as attached to any particular atom in a moiety (e.g. on a particular position along a chain and/or ring) the substituent may replace any H and/or may be located at any available position on the moiety which is chemically suitable and/or effective for the uses described herein.

The invention further relates to a process for the preparation of the polymeric reaction product as described above. The process according to the invention comprises a reaction step wherein compound of formula (I) is brought into contact with a compound according to formula (II) and/or (III), optionally in the presence of a catalyst.

The process according to the invention comprises a reaction step. The purpose of the reaction step is to let a compound of formula (I) react with a compound of formula (II) and/or (III). Thus these compounds must be brought together. The compound according to any of formula (I), (II) and/or (III) may be one single compound or a mixture of two or more compounds falling within the scope of the formulae as defined herein, preferably is two or more compounds.

The product of the process of the invention is a polymeric mixture of compounds i.e. the product has a polydispersity greater than 1.

It may be beneficial to execute the reaction step according to the invention in a solvent or dispersant. As solvents, those compounds are suitable in which the reactants dissolve sufficiently to let the reaction take place. Examples of such solvents are water and various organic solvents. Depending on the specific compound or compounds of formula (I), (II) and/or (III), it may well be possible to use one or more of the reactants as solvent; in such a case, it can be possible to forego on the use of a solvent that is essentially a non-reactant and to execute the reaction step in bulk. In particular, many of the compounds according to formula (I) and in particular according to formula (II) and/or (III) are a liquid at temperatures between 10° C. and 130° C. and can act as dispersant/solvent as well as reactant.

Although the reaction step may proceed spontaneously once the respective compounds have been brought together, it may be useful to bring the compounds together in the presence of a catalyst in order to accelerate the reaction. As catalyst, preferably an acid or a base is used; in particular, a Lewis or a Brønsted type of acid is preferred.

Preferably the catalyst is selected from those having a pKa of 3 or higher. Examples of suitable catalysts include, for example, acetic acid, benzoic acid, formic acid, adipic acid, glutaric acid, linoleic acid, stearic acid, combinations thereof and/or mixtures thereof.

Suitable examples of basic catalysts include trimethyl amine, triethyl amine, DABCO (diaza-bicyclo-octane), DBU (diaza-bicyclo-undecene), DMAP (4-dimethylaminopyridine), sodium hydroxide, potassium hydroxide, and combinations thereof.

Preferably the pH of the reaction mixture is between 1 and 12, preferably to between 2 and 10, in particular to between 3 and 9.

The temperature in the reaction step of present process can vary within wide limits, and preferably lies between 10° C. and 130° C. More preferably the process is carried out at between 40° C. and 120° C. The pressure in the present process preferably is between 0.005 MPa and 1.0 MPa, preferably between 0.02 MPa and 0.2 MPa; most preferably, the pressure is atmospheric.

In the process for the preparation of the polymeric product according to the invention, the molar ratio between the compound (or total amount of compound If more than one) according to formula (II) and/or (III) (E) and the compound or total amount of compound if more than one) according to formula (I) (H), herein referred to as E/H ratio, may vary between wide limits. Preferably, the E/H ratio lies between about 0.1 and about 10, more preferably between about 0.5 and about 3.

The invention further relates to compound(s) according to formula (I) wherein at least one of $R_1$, $R_2$, $R_3$ and $R_4$ is independently compound(s) according to formula (II) and/or (III). Preferably $R_1$ and/or $R_4$ are independently compound(s) according to formula (II) and/or (III).

This adduct may be further reacted to form a polymeric structure. Therefore the present invention also comprises the following repeat unit:

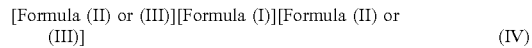

[Formula (II) or (III)][Formula (I)][Formula (II) or (III)]  (IV)

It will be understood that in formula (IV) the formulae (I), (II) and (III) represent the equivalent multivalent (usually divalent) moieties of the formulae represented herein, where two or more substituents thereon are replaced by a direct bond to the adjacent repeat unit. Repeat units that terminate the chain have only one free valence compared to the compounds of formulae (I), (II) and (III) herein.

Preferably the repeat unit is as follows:

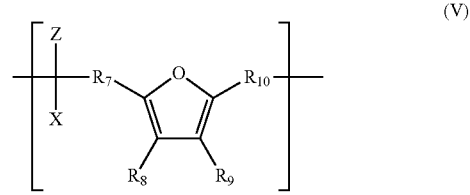

(V)

where Z and X are as defined herein;
$R_8$ and $R_9$ are independently H, OH, substituted or unsubstituted $C_{1-12}$alkyl, substituted or unsubstituted $C_{1-12}$alkenyl, $C_{1-12}$aldehyde, $O_{3-12}$acetal, $C_{2-12}$ether, $C_{2-12}$ester. Preferably $R_8$ and $R_9$ are independently H, OH, substituted or unsubstituted $C_{1-6}$alkyl, and substituted or unsubstituted $C_{1-6}$alkenyl. Preferably $R_8$ and $R_9$ are H, or $C_{1-6}$alkyl;
$R_7$ and $R_{10}$ are independently nil, oxy (—O—), substituted or unsubstituted $O_{1-12}$ alkyl, substituted or unsubstituted $C_{1-12}$alkenyl, $C_{1-12}$aldehyde, $C_{3-12}$acetal, $O_{2-12}$ether, $O_{2-12}$ester. Preferably $R_7$ and $R_{10}$ are independently selected from nil, oxy (—O—), $C_{1-6}$alkyl, $C_{1-6}$alkenyl, $C_{1-6}$-carboxy, hydroxy substituted $C_{1-6}$alkyl, and hydroxy substituted $C_{1-6}$alkenyl. Preferably $R_7$ and $R_{10}$ are independently selected from nil, $CH_2$—CHOH—, —O═O—, and —O(O═O)—.

It will be understood that when a substituent herein (e.g. $R_7$ or $R_{10}$) may be "nil" this means that it is not present and for example the relevant position on the furan moiety is directly attached by a single bond to the adjacent moiety.

The invention further relates to a process for the preparation of a resin. Such processes are as such known and comprise condensation reactions between a furan compound and a compound such as an aldehyde, and typically also subsequent condensation reactions; an example of such a process is the process for preparation of a furan-formaldehyde resin. In the process according to the invention, a compound according to formula (I) is used in the (subsequent) condensation reactions. The (subsequent) condensation reactions may be executed in the same fashion and under similar conditions as described above for the reaction of the compounds according to formulae (I) and (II) or (III), although typically for a, further, prolonged period of time. Polymers according to formula (IV), preferably according to formula (V), are preferably formed.

The resin comprises compounds according to formula I (H). In addition, the resin comprises compounds according to formula II and possibly aldehyde-derived moieties, together referred to as A. The resin thus has a molar A/H ratio. The molar A/H ratio in the resin preferably lies between 0.25 and 3, more preferably between 0.5 and 2.

Resulting from the process as described above, the invention also relates to resins thus obtainable.

Polymers of the present invention may be prepared by one or more suitable polymer precursor(s) which may be organic and/or inorganic and comprise any suitable (co)monomer(s), (co)polymer(s) [including homopolymer(s)] and mixtures thereof which comprise moieties which are capable of forming a bond with the or each polymer precursor(s) to provide chain extension and/or cross-linking with another of the or each polymer precursor(s) via direct bond(s) as indicated herein.

Polymer precursors of the invention may comprise one or more other monomer(s), oligomer(s), polymer(s); mixtures thereof and/or combinations thereof which have suitable polymerisable functionality.

A monomer is a substantially monodisperse compound of a low molecular weight (for example less than one thousand daltons) which is capable of being polymerised. A polymer is a polydisperse mixture of macromolecules of large molecular weight (for example many thousands of daltons) prepared by a polymerisation method, where the macromolecules comprises the multiple repetition of smaller units (which may themselves be monomers, oligomers and/or polymers) and where (unless properties are critically dependent on fine details of the molecular structure) the addition or removal one or a few of the units has a negligible effect on the properties of the macromolecule. A oligomer is a polydisperse mixture of molecules having an intermediate molecular weight between a monomer and polymer, the molecules comprising a small plurality of monomer units the removal of one or a few of which would significantly vary the properties of the molecule. Depending on the context the term polymer may or may not encompass oligomer.

Except where indicated herein polymers and/or polymeric polymer precursors of and/or used in the invention can be (co)polymerised by any suitable means of polymerisation well known to those skilled in the art. Examples of suitable methods comprise: thermal initiation; chemical initiation by adding suitable agents; catalysis; and/or initiation using an optional initiator followed by irradiation, for example with electromagnetic radiation (photo-chemical initiation) at a suitable wavelength such as UV; and/or with other types of radiation such as electron beams, alpha particles, neutrons and/or other particles.

The substituents on the repeating unit of a polymer and/or oligomer may be selected to improve the compatibility of the materials with the polymers and/or resins in which they may be formulated and/or incorporated for the uses described herein. Thus the size and length of the substituents may be selected to optimise the physical entanglement or interlocation with the resin or they may or may not comprise other reactive entities capable of chemically reacting and/or cross-linking with such other resins as appropriate.

The invention moreover relates to the use of the resin according to the invention for the preparation of coatings or shaped articles such as wood-based panels like particle boards and laminates, or mineral wool such as stone wool or glass wool, or in the foundry industry for producing, for example, sand cores. To this end, the resins may be used by methods and under conditions similar to those known per se from the use of known for furan resins. A catalyst and other additives may be added to the resin before the resin is used for processing in its final application. Examples of customary additives are mould release agents, antistatic agents, adhesion promoters, plasticizers, colour enhancing agents, flame retardants, fillers, flow promoters, colorants, diluents, polymerization initiators, UV-stabilizers and heat stabilizers. Examples of fillers are glass fibres, mica, carbon fibres, metal fibres, clay, aramide fibres and strong polyethylene fibres.

Unless the context clearly indicates otherwise, as used herein plural forms of the terms herein are to be construed as including the singular form and vice versa.

The term "comprising" as used herein will be understood to mean that the list following is non-exhaustive and may or may not include any other additional suitable items, for example one or more further feature(s), component(s), ingredient(s) and/or substituent(s) as appropriate.

The terms 'effective', 'acceptable' 'active' and/or 'suitable' (for example with reference to any process, use, method, application, preparation, product, material, formulation, compound, monomer, oligomer, polymer precursor, and/or polymers of the present invention and/or described herein as appropriate) will be understood to refer to those features of the invention which if used in the correct manner provide the required properties to that which they are added and/or incorporated to be of utility as described herein. Such utility may be direct for example where a material has the required properties for the aforementioned uses and/or indirect for example where a material has use as a synthetic intermediate and/or diagnostic tool in preparing other materials of direct utility. As used herein these terms also denote that a functional group is compatible with producing effective, acceptable, active and/or suitable end products.

Many other variations embodiments of the invention will be apparent to those skilled in the art and such variations are contemplated within the broad scope of the present invention.

Further aspects of the invention and preferred features thereof are given in the claims herein.

EXAMPLES

The present invention will now be described in detail with reference to the following non limiting examples which are by way of illustration only. Unless otherwise specified, all parts, percentages and ratios are on a weight basis.

Example 1

Resin Based on Furfuryl Alcohol (FA) and Glyoxylic Acid (GLA)

An amount of GLA (37.0 g, 0.5 mole) was mixed with 49.5 g FA (0.5 mole), and 0.01 g sodium hydroxide (0.25 mmole) was dissolved into the mixture. The temperature of the reaction mixture was increased from room temperature to 80° C. while stirring. After reacting for 1 hour, the reaction mixture was cooled to room temperature. A dark coloured viscous reaction mixture was obtained. The resin could be cured (1 g aliquot) to form an insoluble material by adding a strong acidic catalyst (sulphuric acid, 0.01 g).

Example 2

Resins Based on Furfuryl Alcohol (FA) and Glyoxylic Acid Methyl Ester Hemiacetal (GMHA)

An amount of GMHA (14.2 g, 0.118 mole) was mixed with 5.8 g FA (0.059 mole). The reaction temperature was increased from room temperature to 110° C. After reacting for 6 hours the reaction mixture was cooled to room temperature. GPC analysis showed an increase in molecular weight (Mn ca 900 g/mole). The resin appeared to be dilutable in water (10% wt/wt).

Example 3

Curing of Furan Glyoxylate Resin (Example 2)

The resin (10 g) obtained from experiment 2 was diluted with 10 g demineralised water. Ammonium nitrate (0.2 g) was dissolved into the diluted resin and the mixture was heated to 180° C. After 5 minutes reaction time, a water insoluble solid was obtained.

Example 4

The following composition may be prepared analogously to the method described in the Examples above, to produce a stable resin mixture at a pH of approximately 4.4.

TABLE 4a

| Ingredients | | |
|---|---|---|
| Name | $M_w$ (g/mole) | purity (%) |
| Furfuryl alcohol | 98.1 | 100 |
| Glyoxylic acid (50%) | 74.04 | 50 |
| Oxalic acid dihydrate | 126.07 | 100 |
| $H_2O$ | 18.01 | 100 |
| p-Toluenesulfonic acid hydrate | 18.01 | 100 |
| Ammonia 35% | 17.03 | 35 |
| Pentaerythritol | 136.14 | 100 |

TABLE 4b

| Reactor load | | | |
|---|---|---|---|
| Chemical | m (g) | % (g) | mole |
| Furfuryl alcohol | 196.2 | 84.13 | 2 |
| Glyoxylic acid (50%) | 37.02 | 15.87 | 0.25 |
| Total | 233.22 | 100 | 2.25 |

Ratio FA/GLA is 8

TABLE 4c

| Reactor content | | | |
|---|---|---|---|
| Chemical | m (g) | % | mole |
| Furfuryl alcohol | 196.2 | 84.13 | 2 |
| Glyoxylic acid | 18.51 | 7.94 | 0.25 |
| $H_2O$ | 18.51 | 7.94 | 1.03 |
| Total | 233.22 | 100 | 3.28 |

The acid value of the resultant resin is 60.14 mg KOH/g.

The cured resin (Example 4) of the invention has a greater mechanical strength that the equivalent made without GLA (Comp A), as can be shown by the relative ease with which Comp A breaks by hand compared to Example 4.

The invention claimed is:

1. A polymeric reaction product having the following repeat unit of formula (V):

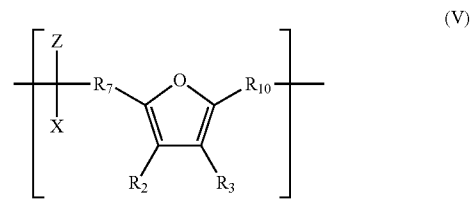

where:
R$_2$ and R$_3$ are independently H, OH substituted or unsubstituted C$_{1-12}$alkyl, substituted or unsubstituted C$_{1-12}$alkenyl, C$_{1-12}$aldehyde, C$_{3-12}$acetal, C$_{2-12}$ether, or C$_{2-12}$ester;
R$_7$ and R$_{10}$ are independently nil, —O—, substituted or unsubstituted C$_{1-12}$alkyl, substituted or unsubstituted C$_{1-12}$alkenyl, C$_{1-12}$aldehyde, C$_{3-12}$acetal, C$_{2-12}$ether, or C$_{2-12}$ester;
X is H or C$_{1-4}$alkyl; and
Z is an electron-withdrawing group.

2. The polymeric reaction product according to claim 1 which is formed at a reaction temperature of between 40° C. and 120° C. by reaction of:
(i) a compound according to formula (I):

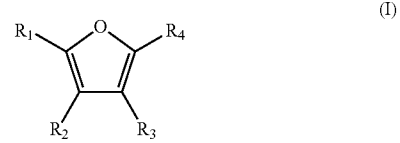

wherein R$_1$ and R$_4$ are independently H, OH, substituted or unsubstituted C$_{1-12}$alkyl, substituted or unsubstituted C$_{1-12}$alkenyl, C$_{1-12}$aldehyde, C$_{3-12}$acetals, C$_{2-12}$ether, or C$_{2-12}$ester; and
wherein at least one of R$_1$, R$_2$, R$_3$ and R$_4$ is H; and
(ii) at least one compound according to formula (II) or (III):

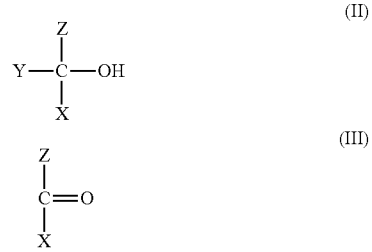

wherein:
X is as defined previously;
Y is selected from the group consisting of OH and OR$_5$ where R$_5$ is a C$_{1-18}$hydrocarbon; and
Z is an electron-withdrawing group which draws electrons away from the atom to which Z is attached.

3. The polymeric reaction product according to claim 2, wherein in formula (II) and/or (III):

Y is OH or $OR_5$ where $R_5$ is $C_{1-12}$alkyl, $C_{3-12}$aryl, $C_{4-12}$aralkyl or $C_{3-12}$cycloalkyl; and Z is an acid, ester, carbonyl, cyano, di-alkylacetal, aldehyde, substituted phenyl, trihalomethyl and/or halo group.

4. The polymeric reaction product according to claim 3, wherein Z is a carboxy and/or a carbonyloxy group.

5. The polymeric reaction product according to claim 2, where $R_1$, $R_2$, $R_3$ and $R_4$ are independently H, $C_{1-6}$alkyl, $C_{1-6}$alkenyl, carboxy substituted $C_{1-5}$alkyl, carboxy substituted $C_{1-5}$alkenyl, hydroxy substituted $C_{1-6}$alkyl, or hydroxy substituted $C_{1-6}$alkenyl.

6. The polymeric reaction product according to claim 2, where $R_1$, $R_2$, $R_3$ and $R_4$ are independently H, —$CH_3$, —$CH_2OH$, —CH=O, or —COOH.

7. The polymeric reaction product according to claim 2, where $R_1$ and $R_4$ are independently H, —$CH_3$, —$CH_2OH$, —CH=O, or —COOH and $R_2$ and $R_3$ are H.

8. The polymeric reaction product according to claim 2, wherein the compound of formula (I) is at least one compound selected from the group consisting of furan, furfural, furfuryl alcohol, hydroxy methyl furan, bis-hydroxy methyl furan, furan dicarboxylic acid, furan carboxylic acid, hydroxymethyl furfunal, hydroxymethyl furan carboxylic acid and combinations or mixtures thereof.

9. The polymeric reaction product according to claim 2, wherein Z is —C(=O)$OR_6$, wherein $R_6$ is H or a $C_{1-12}$ alkyl.

10. The polymeric reaction product according to claim 2, wherein the compound according to formula (II) is a compound of the formula:

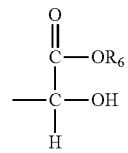

where $R_6$ is H or a $C_{1-12}$ alkyl.

11. The polymeric reaction product according to claim 2, wherein the compound according to formula (II) is a compound of the formula:

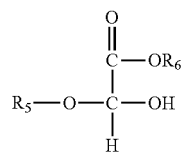

where $R_6$ is H or a $C_{1-12}$ alkyl.

12. The polymeric reaction product according to claim 2, wherein the compound of formula (II) is at least one selected from the group consisting of: glyoxylic acid, pyruvic acid, methylglyoxylate, ethylglyoxylate, methyl pyruvate, ethyl pyruvate, methylglyoxylate methanol hemiacetal, ethylglyoxylate ethanol hemiacetal, ethylglyoxylate methanol hemiacetal, butylglyoxylate butanol hemiacetal, butylglyoxylate methanol hemiacetal, butylglyoxylate ethanol hemiacetal, isopropylglyoxylate isopropanol hemiacetal, propylglyoxylate propanol hemiacetal, cyclohexylglyoxylate methanol hemiacetal, 2-ethylhexylglyoxylate methanol hemiacetal and combinations or mixtures thereof.

\* \* \* \* \*